United States Patent [19]

Campbell et al.

[11] 4,237,138
[45] Dec. 2, 1980

[54] ANTIHYPERTENSIVE 4-AMINO-2-[4-(SUBSTITUTED-ALKOXY)-PIPERIDINO)]QUINAZOLINES

[75] Inventors: Simon F. Campbell, Deal; John C. Danilewicz, Ash, Nr. Canterbury; Colin W. Greengrass, Sandwich, all of England

[73] Assignee: Pfizer Inc., New York, N.Y.

[21] Appl. No.: 30,003

[22] Filed: Apr. 16, 1979

Related U.S. Application Data

[63] Continuation-in-part of Ser. No. 960,628, Nov. 14, 1978, abandoned.

[30] Foreign Application Priority Data

Nov. 16, 1977 [GB] United Kingdom ............... 47583/77
Oct. 4, 1978 [DK] Denmark ............... 4403/78
Jan. 31, 1979 [GB] United Kingdom ............... 03398/79

[51] Int. Cl.³ ............... A61K 31/505; C07D 401/04
[52] U.S. Cl. ............... 424/251; 544/291; 546/216
[58] Field of Search ............... 544/291; 424/251

[56] References Cited

U.S. PATENT DOCUMENTS 3,511,836  5/1970  Hess ............... 544/291

*Primary Examiner*—Paul M. Coughlan, Jr.
*Attorney, Agent, or Firm*—Connolly and Hutz

[57] ABSTRACT

Regulators of the cardiovascular system and, in particular, in the treatment of hypertension having the formula

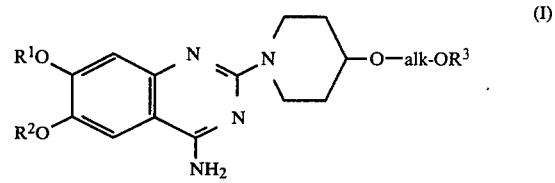

pharmaceutically-acceptable bioprecursors thereof, and the pharmaceutically-acceptable acid addition salts thereof; wherein each of $R^1$ and $R^2$ is $C_{1-4}$ alkyl or $-CH_2CF_3$; alk is ethylene, monophenyl substituted ethylene, mono- and dimethyl substituted ethylene or monophenylmonomethyl substituted ethylene; and $R^3$ is hydrogen, $C_{1-4}$ alkyl, $C_3$-$C_6$ cycloalkyl; phenyl or substituted phenyl; and methods for their preparation.

11 Claims, No Drawings

ANTIHYPERTENSIVE 4-AMINO-2-[4-(SUBSTITUTED-ALKOXY)-PIPERIDINO)]QUINAZOLINES

CROSS REFERENCE TO RELATED APPLICATION

This application is a continuation-in-part of application Ser. No. 960,628, filed Nov. 14, 1978, now abandoned.

BACKGROUND OF THE INVENTION

1. Field of the Invention

This invention relates to therapeutic agents which are novel derivatives of 4-amino-2-piperidinoquinazoline, and is particularly concerned with derivatives having a substituted alkoxy group in the 4-position of the piperidino group. Such compounds are useful as regulators of the cardiovascular system and, in particular, in the treatment of hypertension.

2. Description of the Prior Art

The therapeutic properties of a variety of quinazolines, including 4-amino-2-[(4-substituted)piperazin-1-yl]quinazolines are well known. U.S. Pat. No. 3,511,836 describes 4-amino-6,7-dialkoxy-2-[(4-substituted)piperazin-1-yl]quinazolines wherein the 4-substituent is hydroxy, alkoxy or hydroxyalkyl. The products are valuable hypotensive agents.

SUMMARY OF THE INVENTION

The novel compounds according to the invention are those having the general formula:

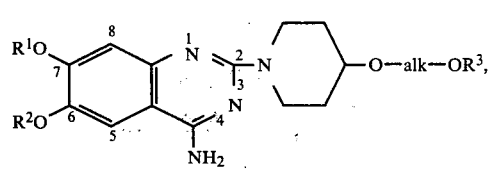

pharmaceutically-acceptable bioprecursors thereof, and the pharmaceutically-acceptable acid addition salts thereof, wherein $R^1$ and $R^2$ is selected from the group consisting of $C_{1-4}$ alkyl and $-CH_2CF_3$; alk is selected from the group consisting of ethylene, monophenyl substituted ethylene, mono- and dimethyl substituted ethylene, and monophenyl-monomethyl substituted ethylene; $C_3-C_6$ cycloalkyl, and

wherein each of X and Y is selected from the group consisting of hydrogen, $C_{1-4}$ alkyl, $C_{1-4}$ alkoxy, halogen, $CF_3$, $-CONR^4R^5$ and $-SO_2NR^4R^5$ wherein each of $R^4$ and $R^5$ is selected from the group consisting of hydrogen and $C_{1-4}$ alkyl.

In this specification, "halogen" means fluorine, chlorine, bromine or iodine. In compounds of this invention wherein the alkyl or alkoxy groups contain 3 or more carbon atoms, said groups may be straight or branched chain.

Pharmaceutically-acceptable acid addition salts are those formed from acids which form non-toxic acid addition salts containing pharmaceutically acceptable anions, such as the hydrochloride, hydrobromide, sulphate or bisulphate, phosphate or acid phosphate, acetate, maleate, fumarate, lactate, tartrate, citrate, gluconate, saccharate or p-toluenesulphonate salts.

The compounds of the invention containing one or more asymmetric centers will exist as one or more pairs of enantionmers, and such pairs, or individual isomers can be separated by physical methods, e.g. by fractional crystallization of suitable salts. The invention includes the separated pairs as well as mixtures thereof, as racemic mixtures or as separated d- and l-optically active isomeric forms.

A preferred group of compounds of formula I comprises those wherein each of $R^1$ and $R^2$ is methyl; $-O-$alk$-OR^3$ is $-OCH_2CH_2OR^3$,

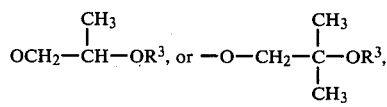

and $R^3$ is preferably hydrogen, $C_1-C_4$ alkyl, cyclopentyl, or phenyl optionally substituted by $C_{1-4}$ alkyl, $C_{1-4}$ alkoxy, halogen, trifluoromethyl or carbamoyl.

In one preferred group of compounds $R^3$ is other than $C_3-C_6$ cycloalkyl and X and Y are other than trifluoromethyl.

The two preferred individual compounds are those in which (a) each of $R^1$ and $R^2$ is $CH_3$, "alk" is $-CH_2CH_2-$ and $R^3$ is $C_2H_5$ and (b) each of $R^1$ and $R^2$ is $CH_3$, "alk" is $-CH_2CH_2-$ and $R^3$ is phenyl.

DETAILED DESCRIPTION OF THE INVENTION

The compounds of the invention can be prepared by a number of routes, including the following:

(1) The compounds can be prepared by reacting a quinazoline of the formula:

wherein Q represents a facile leaving group such as chloro, bromo, iodo, $C_{1-4}$ alkoxy, ($C_{1-4}$ alkyl)thio or ($C_{1-4}$ alkyl) sulphonyl, with a piperidine of the formula:

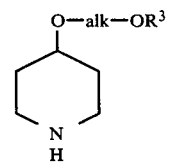

Q is preferably chloro or bromo.

Typically the reaction is carried out in the presence of a base such as triethylamine or excess reagent of the formula (III).

In a typical procedure the reactants are heated together, e.g. at a temperature of 70° to 130° C., preferably under reflux, in an inert organic solvent, e.g. n-butanol, for periods of up to about 48 hours. The product can be isolated and purified by conventional procedures.

For example, the product is typically obtained in crude form by evaporation of the reaction mixture in vacuo, and the crude product purified either by recrystallization from a suitable solvent, or by conversion to e.g. the hydrochloride salt by reaction with hydrogen chloride in e.g. ethanol followed by recrystallization of the salt. In some cases of course the product of the reaction will be the hydrochloride salt. In some cases also the crude product can be purified chromatographically, e.g. by basifying it and extracting with chloroform, evaporating the chloroform extracts, and chromatographing the residue on e.g. neutral alumina, the product being eluted with chloroform or with a mixture of chloroform and methanol. The eluted product can be purified by conversion to the hydrochloride salt followed by recrystallization, as above.

The intermediates of the formula (II) are in general known compounds or can be prepared by methods analogous to those of the prior art.

The intermediates of the formula (III) are either known compounds or can be prepared by conventional methods, e.g. as follows:

(a)

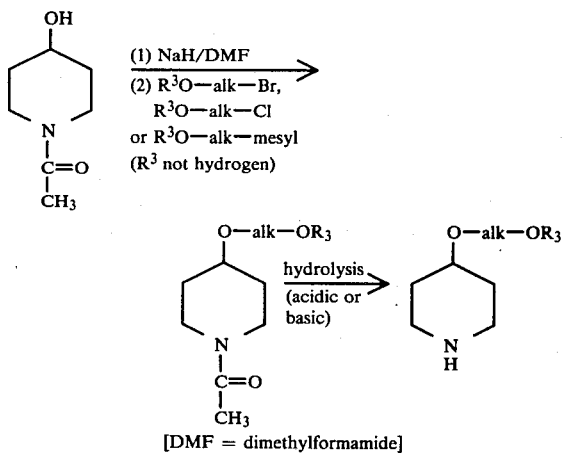

[DMF = dimethylformamide]

(b) The piperidines in which "alk" is an ethylene group substituted by 1 or 2 lower alkyl groups are also preparable via the corresponding 1-acetyl-4-alkenoxypiperidines, e.g. as follows ($R^3$ can be hydrogen in this route):

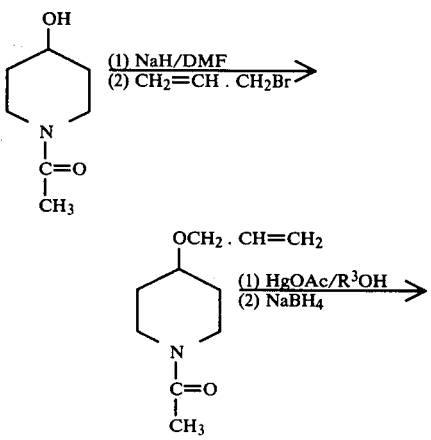

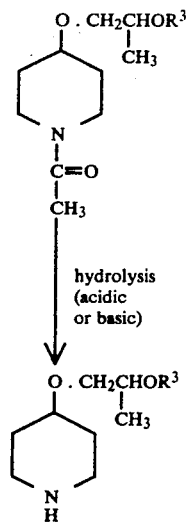

(c) 4-(2-Hydroxyethoxy)piperidine can be prepared by the previously described route:

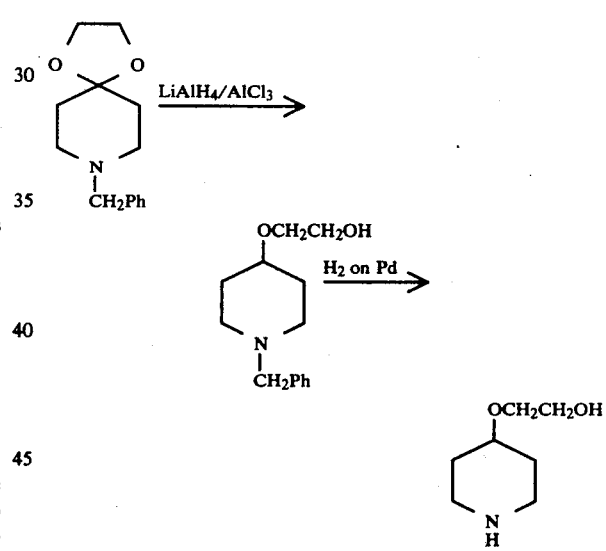

(d) 4-(2-Hydroxyalkoxy)piperidines can also be prepared by the following conventional routes:

e.g.
(i)

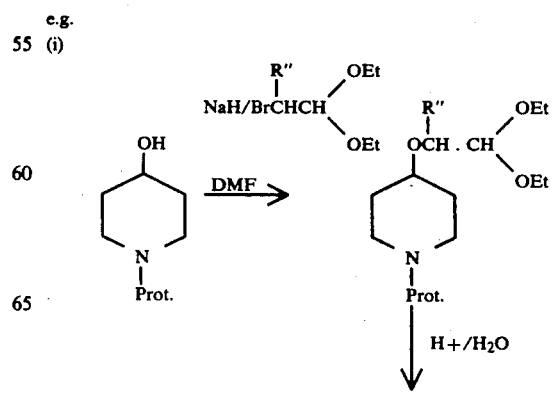

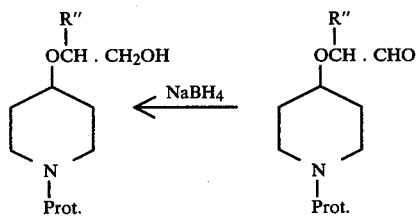

[In which Prot. is a suitable N protecting group, for example acetyl or benzyl, and can be removed by conventional methods at the final stage, and R″ is H or lower alkyl]

(ii)

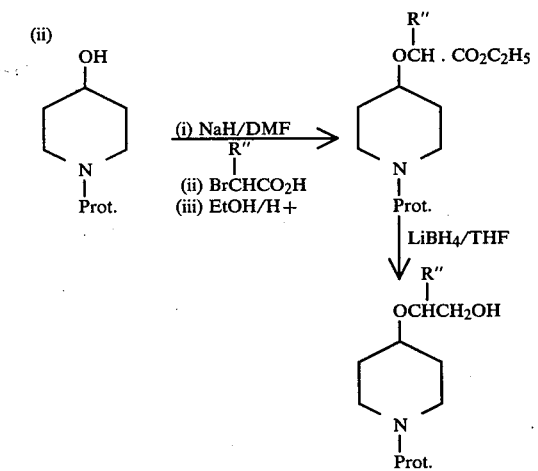

(Prot. and R″ are as defined above)
or (iii)

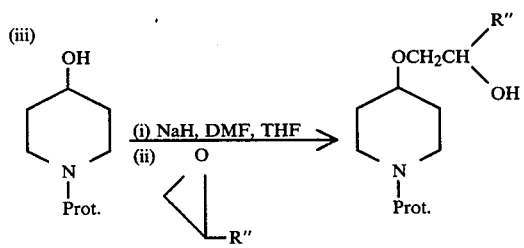

(Prot. and R″ are as defined above)

(e) 4-(2-Alkoxyalkoxy)piperidines can be prepared by reaction of an N-protected 4-(2-hydroxyalkoxy)piperidine obtained by one of the above routes with an alkyl halide or mesylate in the presence of a strong base, e.g.:

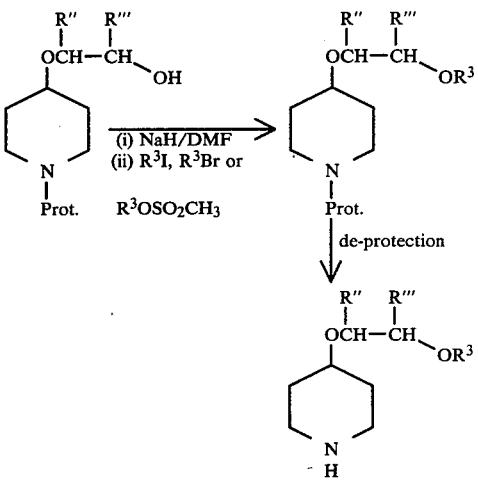

(Prot. and R″ are as defined above;
R‴ = H or lower alkyl)

and (f) 4-(2-Aryloxyalkoxy)piperidines can be prepared by:

(i) Reaction of an N-acetyl-4-(2-hydroxyalkoxy)-piperidine obtained as above with an appropriately substituted phenol in the presence of triphenylphosphine and diethyl azodicarboxylate ("D.E.A.D."):

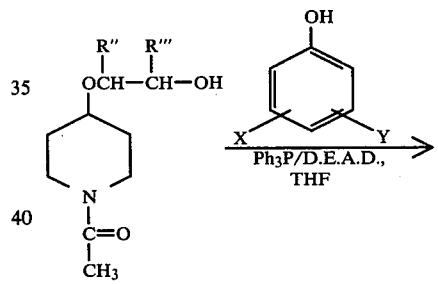

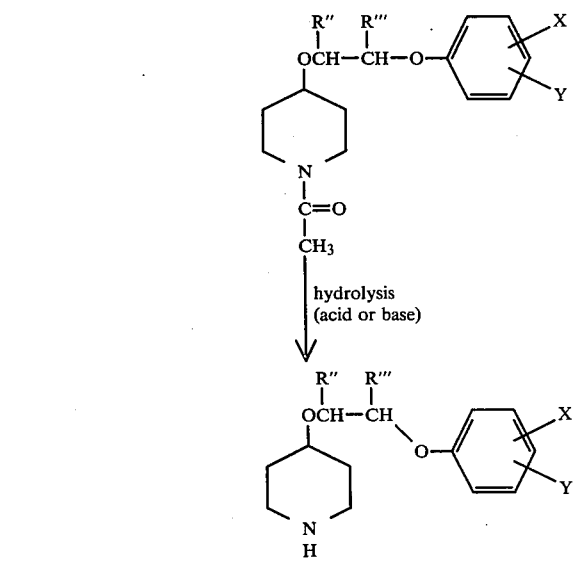

(ii) 4-(2-Aryloxyalkoxy)piperidines can alternatively be prepared from an N-protected-4-(2-hydroxyalkoxy)-piperidine, obtained as above, and fluorobenzene or a substituted fluorobenzene in the presence of NaH and D.M.F.:

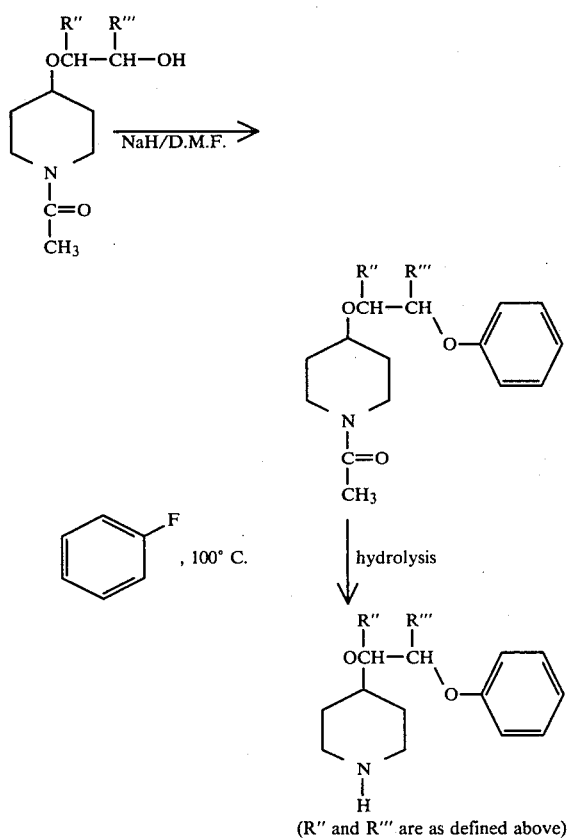

(R" and R'" are as defined above)

(2) The pharmaceutically acceptable acid addition salts of the compounds of the formula (I) can be prepared by conventional procedures, e.g. by mixing the free base with the appropriate acid in a suitable solvent, e.g. iso-propanol, filtering, and if necessary recrystallizing the thus-produced salt to purity. Often of course the product of route (1) will be in the form of an acid addition salt.

The invention also includes the pharmaceutically-acceptable bioprecursors of the compounds of the formula (I) and said salts thereof.

The term "pharmaceutically acceptable bioprecursor" requires some explanation. It is of course, common practice in pharmaceutical chemistry to overcome some undesirable physical or chemical property of a drug by converting the drug into a chemical derivative which does not suffer from that undesirable property, but which, upon administration to an animal or human being, is converted back to the parent drug. For example, if the drug is not well absorbed when given to the animal or patient, by the oral route, it is often possible to convert the drug into a chemical derivative which is well absorbed and which in the serum or tissues is reconverted to the parent drug. Again, if a drug is unstable in solution, it is often possible to prepare a chemical derivative of the drug which is stable and can be administered in solution, but which is reconverted in the body to give the parent drug. The pharmaceutical chemist is well aware of the possibility of overcoming intrinsic deficiencies in a drug by chemical modifications which are only temporary and are reversible upon administration to the animal or patient.

For the purpose of this specification the term "pharmaceutically acceptable bioprecursor" of a compound of the formula (I) means a compound having a structural formula different from the compounds of the formula (I) but which nonetheless, upon administration to an animal or human being, is converted in the patients body to a compound of the formula (I).

The antihypertensive activity of the compounds of the invention is shown by their ability to lower the blood pressure of consciuos spontaneously hypertensive rats and conscious renally hypertensive dogs, when administered orally at doses of up to 5 mg/kg.

The compounds of the invention can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules either alone or in admixture with excipients, or in the form of elixirs or suspensions containing flavoring or coloring agents. They can be injected parenterally, for example, intramuscularly, intravenously or subcutaneously. For parenteral administration, they are best used in the form of a sterile aqueous solution which can contain other solutes, for example, enough salts or glucose to make the solution isotonic.

Thus the invention also provides a pharmaceutical composition comprising a compound of the formula (I) or a pharmaceutically acceptable acid addition salt thereof together with a pharmaceutically acceptable diluent or carrier.

The compounds of the invention can be administered to humans for the treatment of hypertension by either the oral or parenteral routes. They are administered orally at dosage levels approximately within the range 1 to 20 mg./day for an average adult patient (70 kg.), given in a single dose or up to 3 divided doses. Intravenous dosage levels range from about 1/5th to 1/10th of the daily oral dose. For an average adult patient, individual oral doses in tablet or capsule form will be approximately in the range from 5 to 100 mg. of the active compound. Variations will necessarily occur depending on the weight and condition of the subject being treated and the particular route of administration chosen as will be known to those skilled in the art.

The invention yet further provides a method of treating an animal, including a human being, having hypertension, which comprises administering to the animal an antihypertensive amount of a compound of the formula (I) or pharmaceutically acceptable acid addition salt thereof or pharmaceutical composition as defined above.

The following Examples illustrate the invention:

EXAMPLE 1

Preparation of 4-Amino-6,7-dimethoxy-2-[4-(2-ethoxyethoxy)-piperidino]quinazoline hydrochloride

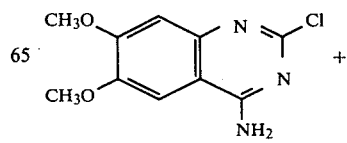
+

-continued thoxyquinazoline and the appropriately substituted piperidine, and were isolated in the form indicated.

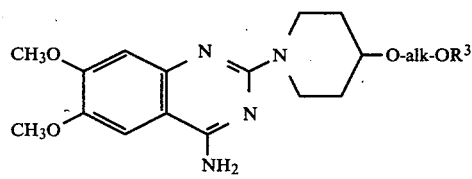

| Example No. | —O-alk-OR³ | Form Isolated and m.p. (°C.) | Analysis (Theoretical in brackets) | | |
|---|---|---|---|---|---|
| | | | C | H | N |
| 2 | —OCH₂CH₂O-n-C₄H₉ | Hydrochloride 199–201° | 57.5 (57.2 | 7.6 7.5 | 12.7 12.7) |
| 3 | —OCH₂C(CH₃)₂—OH | Free base, 204–205° | 61.0 (60.6 | 7.7 7.5 | 14.9 14.9) |
| 4 | —OCH₂—C(CH₃)₂—OC₂H₅ | Hydrochloride monohydrate 244–246° | 54.7 (55.0 | 7.5 7.7 | 12.1 12.2) |
| 5 | —OCH₂CH₂OCH(CH₃)₂ | Free base, 130–134° | 60.9 (61.5 | 7.7 7.7 | 13.8 14.4) |
| 6 | —OCH₂CH(CH₃)—OC₆H₅ | Hydrochloride, 222–223° | 60.1 (60.7 | 6.4 6.6 | 12.0 11.8) |
| 7 | —OCH₂CH₂O—⟨cyclopentyl⟩ | Hydrochloride, 210–211° | 57.9 (58.3 | 7.2 7.4 | 12.4 12.4) |

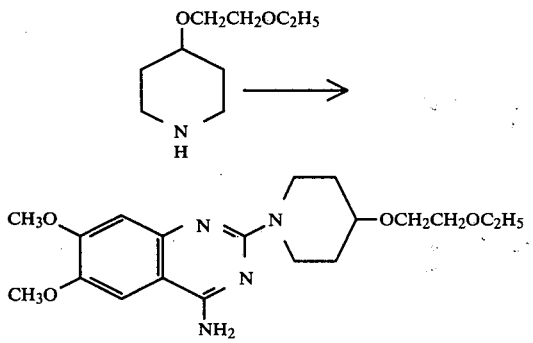

4-Amino-2-chloro-6,7-dimethoxyquinazoline (4.3 g.), 4-(2-ethoxyethoxy)piperidine (3.2 g.) and triethylamine (10 ml.) in n-butanol (400 ml.) were heated at reflux overnight under an atmosphere of nitrogen. The mixture was then cooled, evaporated in vacuo, and the residue basified (aqueous Na₂CO₃) and extracted 3 times with chloroform. The combined chloroform extracts were evaporated and the residue chromatographed on neutral alumina (150 g., Grade I, deactivated with 5 ml water). Elution with chloroform gave the crude product (3.6 g.) which was converted to the hydrochloride salt by treatment with hydrogen chloride in ethanol. The hydrochloride was then recrystallized from ethanol/isopropanol to give 4-amino-6,7-dimethoxy-2-[4-(2-ethoxyethoxy)piperidino]quinazoline hydrochloride (3.4 g.), m.p. 219°–220° C.

Analysis %: Found: C, 55.4; H, 7.2; N, 13.5. Calculated for C₁₉H₂₈N₄O₄.HCl: C, 55.3; H, 7.1; N, 13.6.

EXAMPLES 2–7

The following quinazolines were prepared similarly to Example 1, starting from 4-amino-2-chloro-6,7-dime- The following minor differences in procedure from Example 1 should be mentioned. In Example 3, the product from the chromatographic purification was recrystallized directly without prior conversion to a hydrochloride salt. In Examples 5 and 7, silica was used for the chromatographic purification. In Example 6, the residue remaining after the evaporation of the original reaction mixture (which was a hydrochloride salt) was recrystallized from dimethylformamide and then directly chromatographed on silica.

EXAMPLE 8

4-Amino-6,7-dimethoxy-2-[4-(2-methoxy-n-propoxy)-piperidino]quinazoline hydrochloride 4-Amino-2-chloro-6,7-dimethoxyquinazoline (3.6 g.), 4-(2-methoxy-n-propoxy)piperidine (3.0 g.) and triethylamine (1.5 g.) in n-butanol were heated under reflux for 30 hours. The solvent was evaporated in vacuo, the residue stirred with diethyl ether, the solid collected and recrystallized twice from isopropanol to give 4-amino-6,7-dimethoxy-2-[4-(2-methoxy-n-propoxy)-piperidino]quinazoline hydrochloride (2.8 g.), m.p. 239°–241° C.

Analysis %: Found: C, 55.1; H, 7.2; N, 13.6. Calculated for C₁₉H₂₈N₄O₄.HCl:C, 55.2; H, 7.1; N, 13.6.

EXAMPLES 9–22

The following quinazolines were prepared similarly to Example 8, starting from 4-amino-2-chloro-6,7-dimethoxyquinazoline and the appropriately substituted piperidine, and were isolated in the form indicated.

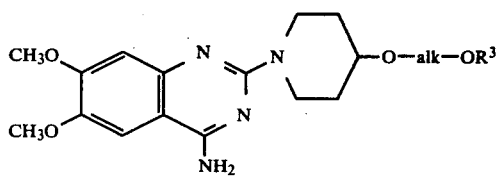

| Example No. | —O—alk—OR³ | Form Isolated and m.p. (°C.) | Analysis (Theoretical in brackets) C | H | N |
|---|---|---|---|---|---|
| 9 | —OCH₂CH₂OH | hydrochloride hemihydrate, 252–253° | 51.8 (51.8 | 6.3 6.7 | 14.1 14.2) |
| 10 | —OCH₂CH₂O—⟨C₆H₄⟩—CH₃ | hydrochloride hemihydrate, 216–217° | 60.0 (59.6 | 6.4 6.7 | 11.8 11.6) |
| 11 | —OCH₂CH₂O—⟨C₆H₄⟩—F | hydrochloride 226–227° | 57.6 (57.7 | 5.9 5.9 | 12.0 11.7) |
| 12 | —OCH₂CH₂O—⟨C₆H₄⟩—OCH₃ | hydrochloride hydrate, 195–196° | 56.8 (56.6 | 6.2 6.5 | 11.1 11.0) |
| 13 | —OCH₂CH₂O—⟨C₆H₃(OCH₃)₂⟩ (2,3-di-OCH₃) | hydrochloride, 203–204° | 57.5 (57.6 | 6.3 6.4 | 10.7 10.8) |
| 14 | —OCH₂CH₂O—⟨C₆H₄⟩—OCH₃ (meta) | hydrochloride hemihydrate, 207–209° | 57.4 (57.7 | 6.3 6.4 | 11.0 11.2) |
| 15 | —OCH₂CH₂O—⟨C₆H₄⟩—CF₃ | hydrochloride, 259–261° | 54.0 (54.5 | 5.4 5.3 | 10.9 10.6) |
| 16 | —OCH₂CH₂O—⟨C₆H₄⟩—CONH₂ | Hydrochloride hemihydrate, 272–273° | 56.4 (56.2 | 5.9 6.1 | 14.0 13.7) |
| 17 | —OCH₂CH₂O—⟨C₆H₄⟩—CONH₂ (meta) | Hydrochloride hydrate, 167–169° | 55.2 (55.2 | 6.2 6.2 | 13.4 13.4) |
| 18 | —OCH₂CH₂OCH₃ | Hydrochloride 220–222° | 53.8 (54.2 | 7.0 6.8 | 14.1 14.0) |
| 19 | —OCH₂CH₂OC₆H₅ | Hydrochloride 232–233° | 59.5 (59.9 | 6.6 6.3 | 12.3 12.2) |
| 20 | —OCH₂CH(CH₃)OH | Hydrochloride hemihydrate 245–246° | 52.8 (53.0 | 6.7 6.7 | 13.7 13.7) |
| 21 | —OCH₂CH(CH₃)—OC₂H₅ | Hydrochloride hemihydrate 217–218° | 55.6 (55.1 | 7.2 7.4 | 12.5 12.8) |
| 22 | —OCH₂C(CH₃)₂·OCH₃ | Hydrochloride 239–242° | 56.0 (56.3 | 7.5 7.3 | 12.8 13.1) |

EXAMPLE 23

Preparation of 4-Amino-6,7-dimethoxy-2-[4-(2-ethoxy-1-phenylethoxy)piperidino]quinazoline hydrochloride 4-Amino-2-chloro-6,7-dimethoxyquinazoline (2.6 g.) and 4-(2-ethoxy-1-phenylethoxy)piperidine (3.0 g.) in n-butanol (100 ml.) were heated under reflux for 22 hours. The solution was then cooled, filtered and the filtrate evaporated in vacuo. The residue was triturated with diethylether and recrystallized twice from isopropanol to give 4-amino-6,7-dimethoxy-2-[4-(2-ethoxy-1-phenyl-ethoxy piperidino]quinazoline hydrochloride (2.0 g.), m.p. 229°–230°.

Analysis %: Found: C, 61.0; H, 6.9; N, 11.5. Calculated for $C_{25}H_{32}N_4O_4 \cdot HCl$: C, 61.4; H, 6.8; N, 11.5.

EXAMPLE 24

Preparation of 4-Amino-6,7-Dimethoxy-2-[4-(2-phenoxy-1-phenylethoxy)piperidino]quinazoline hydrochloride hydrate 4-Amino-2-chloro-6,7-dimethoxyquinazoline (1.44 g.) and 4-(2-phenoxy-1-phenylethoxy)piperidine (2.0 g.) in n-butanol (100 ml.) were heated under reflux for 20 hours. The solvent was then evaporated in vacuo, the residue triturated with ether and crystallized from isopropanol. The solid was partitioned between chloroform and aqueous sodium carbonate solution, the chloroform extract dried ($MgSO_4$) and the solvent evaporated in vacuo. The residue was chromatographed on silica (100 g.) eluting with chloroform followed by chloroform methanol (20:1). Fractions containing the product were combined, the solvent evaporated in vacuo and the residue converted to the hydrochloride salt by treatment of a chloroform solution with ethereal hydrogen chloride.

The solid hydrochloride salt was collected and recrystallized from isopropanol to give 4-amino-6,7dimethoxy-2-[4-(2-phenoxy-1-phenylethoxy)piperidino] quinazoline, hydrochloride hydrate, m.p. 202°–204°.

Analysis %: Found: C, 62.8; H, 6.1; N, 10.0. Calculated for $C_{29}H_{32}N_4O_4 \cdot HCl \cdot H_2O$: C, 62.8; H, 6.4; N, 10.1.

EXAMPLES 25 TO 28

The following compounds were prepared similarly to the previous Examples, starting from 4-amino-2-chloro-6,7-dimethoxyquinazoline and the appropriate piperidine, viz., the product of Example 25 was prepared similarly to Example 23, and the products of Examples 26–28 were prepared similarly to Example 24, but the product of Example 27 was not converted to a hydrochloride salt.

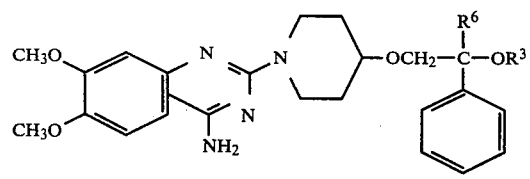

| Example No. | $R^6$ | $R^3$ | Form Isolated and m.p. (°C.) | Analysis % (Theoretical in brackets) C | H | N |
|---|---|---|---|---|---|---|
| 25 | H | H | hydrochloride 241–243° | 59.7 (59.9 | 6.3 6.3 | 12.0 12.2) |

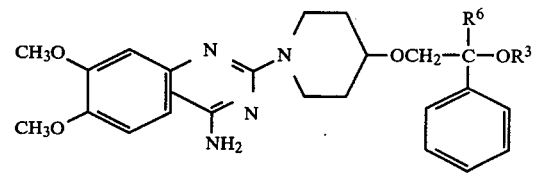

| Example No. | $R^6$ | $R^3$ | Form Isolated and m.p. (°C.) | Analysis % (Theoretical in brackets) C | H | N |
|---|---|---|---|---|---|---|
| 26 | H | $C_2H_5$ | hydrochloride 234–235° | 61.3 (61.4 | 6.7 6.8 | 11.0 11.5) |
| 27 | $CH_3$ | H | free base monohydrate, 146–148° | 63.0 (63.1 | 6.8 7.1 | 12.2 12.3) |
| 28 | $CH_3$ | $C_2H_5$ | hydrochloride 231–233° | 61.9 (62.1 | 7.0 7.0 | 11.1 11.1) |

EXAMPLE 27

The following compounds are prepared from the appropriate 4-amino-2-chloro-6,7-dialkoxyquinazoline and the appropriately substituted piperidine according to the procedure of Example 1.

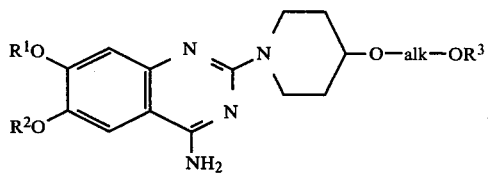

| $R^1$ and $R^2$ | —O-alk-$OR^3$ |
|---|---|
| $C_2H_5$ | $-OCH_2CH_2OC_2H_5$ |
| $i\text{-}C_3H_7$ | $-OCH_2CH_2OC_2H_5$ |
| $n\text{-}C_4H_9$ | $-OCH_2CH_2OC_2H_5$ |
| $n\text{-}C_3H_7$ | $-OCH_2CH_2-OC_6H_5$ |
| $C_2H_5$ | $-OCH_2CH(CH_3)OC_6H_5$ |
| $n\text{-}C_4H_9$ | $-OCH_2C(CH_3)_2OC_2H_5$ |
| $C_2H_5$ | $-OCH_2CH_2OCH(CH_3)_2$ |
| $sec\text{-}C_4H_9$ | $-OCH_2CH_2-(4\text{-}FC_6H_4)$ |
| $C_2H_5$ | $-OCH_2CH_2-(4\text{-}CH_3C_6H_4)$ |
| $n\text{-}C_3H_7$ | $-OCH_2CH_2O-[2,6\text{-}(CH_3O)_2C_6H_3]$ |
| $C_2H_5$ | $-OCH_2CH_2O-(3\text{-}H_2NCOC_6H_4)$ |
| $C_2H_5$ | $-OCH_2C(CH_3)_2OCH_3$ |
| $n\text{-}C_4H_9$ | $-OCH_2CH(CH_3)OH$ |
| $i\text{-}C_3H_7$ | $-OCH_2CH_2-OC_5H_9$ |

The following Examples illustrate the preparation of certain of the starting materials used in the previous Examples:

EXAMPLE A

Preparation of 4-(2-Methoxyethoxy)piperidine

A solution of N-acetyl-4-hydroxypiperidine (30.5 g.) in dimethylformamide (200 ml.) was added dropwise to a stirred suspension of sodium hydride (11.26 g., 50% dispersion in mineral oil) in dimethylformamide (300 ml.) under an atmosphere of nitrogen. The reaction temperature was kept below 30° C. by external cooling and, after the addition was complete, stirring was continued for a further 1¼ hours. A solution of 1-bromo-2-methoxyethane (32.6 g.) in dimethylformamide (100 ml.) was then added dropwise with external cooling, and the resulting clear solution was stirred at room temperature overnight. The reaction mixture was then evaporated in vacuo, the residue partitioned between water and chloroform, the organic extracts dried (Na₂SO₄) and evaporated to leave a crude residue (16.1 g.). The above aqueous phase was saturated with sodium chloride, further extracted with chloroform, and the organic phase was dried (Na₂SO₄), and evaporated to leave a further residue (9.2 g.). This residue was combined with the original residue and heated on a steam bath overnight with hydrochloric acid (243 ml., 2N). The reaction mixture was extracted with chloroform to remove residual mineral oil, the aqueous phase concentrated, basified with sodium hydroxide (pH 12), then reextracted with chloroform. The organic extracts were washed with brine, dried (Na₂SO₄) and evaporated to leave 4-(2-methoxyethoxy)piperidine (8.3 g.). A sample of this product in ethyl acetate was converted to the oxalate salt by the addition of ethereal oxalic acid followed by recrystallization from ethanol, the oxalate having an m.p. of 86°–88° C.

Analysis %: Found: C, 48.1; H, 7.6; N, 5.6. Calculated for $C_8H_{17}NO_2 \cdot (CO_2H)_2$: C, 48.2; H, 7.7; N, 5.6.

The following piperidine derivatives were prepared by procedures similar to that of Example A, starting from N-acetyl-4-hydroxypiperidine and the appropriate bromide. Hydrolysis of the N-acetylated intermediates in Examples B and D was carried out using dilute sodium hydroxide in place of dilute hydrochloric acid.

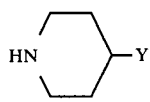

| Example | Y | Form Isolated and m.p. (°C.) | Analysis % (Theoretical in brackets) | | |
|---|---|---|---|---|---|
| | | | C | H | N |
| B | —OCH₂CH₂OC₆H₅ | Oxalate 144–145° | 58.5 (57.9 | 6.8 6.8 | 4.3 4.5) |
| C | —OCH₂CH₂O-n-C₄H₉ | Oxalate hemihydrate 86–88° | 52.4 (52.0 | 8.4 8.7 | 4.8 4.7) |
| D | —OCH₂CH₂OC₂H₅ | Oxalate 93–95° | 50.5 (50.2 | 8.2 8.0 | 5.2 5.3) |

EXAMPLE E

Preparation of N-Acetyl-4-allyloxypiperidine

A solution of N-acetyl-4-hydroxypiperidine (100 g.) in dimethylformamide (250 ml.) was added dropwise to sodium hydride (38 g., 50% mineral oil dispersion) under an atmosphere of nitrogen. The mixture was stirred for 2 hours then allyl bromide (93 g.) was added slowly whilst maintaining the reaction temperature at 25° C. by external cooling. The mixture was then stirred at room temperature overnight, diluted with isopropanol (20 ml) and ether (500 ml.), filtered, and evaporated in vacuo. Distillation of the residue gave N-acetyl-4-allyloxypiperidine (108.8 g.), b.p. 128° C./2 mm., identified spectroscopically.

EXAMPLE F

Preparation of 4-(2-Ethoxy-n-propoxy)piperidine

A solution of N-acetyl-4-allyloxypiperidine (6.4 g.) in absolute ethanol (10 ml.) was added dropwise to a stirred suspension of mercuric acetate (11.5 g.) in ethanol (50 ml.) at room temperature. After 20 minutes the mercuric acetate had dissolved and the mixture was stirred for a further 40 minutes, cooled in ice-water, and sodium hydroxide (20 ml., 5N) was then added. A yellow precipitate formed during the addition. A solution of sodium borohydride (1.3 g.) in sodium hydroxide (20 ml., 5N) was then added, the mixture stirred for 10 minutes, and acetic acid added to bring the pH to 6. The mixture was filtered from precipitated mercury, the ethanol evaporated in vacuo, and the resulting aqueous phase extracted with chloroform.

The organic extracts were dried (Na₂SO₄), evaporated in vacuo, and the resulting crude residue (7.5 g.) taken up in ethanol (50 ml.) and heated under reflux overnight with sodium hydroxide (20 ml., 5N) and water (20 ml.). Most of the ethanol was then removed in vacuo, the aqueous layer extracted with ether, the extracts dried (Na₂SO₄) and evaporated to leave a residue (5 g.). Thin layer chromatography indicated incomplete hdyrolysis of the acetyl function had occurred so the residue was treated with hydrochloric acid (20 ml., 2N) and heated on a steam bath for 10 hours. The mixture was then washed with ether, the aqueous phase basified (Na₂CO₃), extracted with ether and the organic extract dried (Na₂SO₄) and evaporated to leave a residue (4.3 g.). Distillation of the residue gave 4-(2-ethoxy-n-propoxy)piperidine (3.0 g.), b.p. 112°–116° C./10 mm., from which sesquioxalate salt was prepared by reacting an ethereal solution of the piperidine with ethereal oxalic acid, followed by recrystallization from ethyl acetate, the oxalate having an m.p. of 68°–70° C.

Analysis %: Found: C, 48.3; H, 7.5; N, 4.7. Calculated for $C_{10}H_{21}NO_2 \cdot 1.5(CO_2H)_2$: C, 48.4; H, 7.5; N, 4.4.

EXAMPLE G

Preparation of 4-(2-Hydroxy-n-propoxy)piperidine

N-Acetyl-4-allyloxypiperidine (18 g.) in tetrahydrofuran (30 ml.) was added dropwise to a stirred yellow suspension of mercuric acetate (34 g.) in a mixture of water (120 ml.) and tetrahydrofuran (120 ml.). The suspension dissolved during the addition and the resulting clear solution was stirred at room temperature for 20 minutes, then sodium hydroxide (70 ml., 5N) was added, accompanied by ice/water cooling. The intermediate thus obtained was then reduced by the addition of sodium borohydride (2 g.) in sodium hydroxide (40 ml., 5N), the excess hydride being destroyed after 10 minutes with glacial acetic acid. The liquid phase was then decanted off, saturated with sodium chloride, the organic phase separated, and the remaining aqueous layer extracted four times with chloroform. The combined organic phases were dried (Na₂SO₄), and evaporated in vacuo to leave a colorless oil (23 g.).

This oil was stirred with 5N sodium hydroxide at room temperature for 16 hours, then at 100° C. for 2 hours. The solution was then extracted with chloroform (four times), the combined extracts dried (Na₂SO₄), and evaporated in vacuo to leave a crude crystalline product (16.1 g.). This was taken up in methylene chloride, filtered, evaporated, and the residue triturated with petroleum ether (b.p. 40°/60° C.) to yield 4-(2-hydroxy-n-propoxy)piperidine (11.0 g.), m.p. 55°–57° C. The oxalate salt thereof was prepared as in Example F and recrystallized from isopropanol, m.p. 104°–105° C.

Analysis %: Found: C, 48.2; H, 7.7; N, 5.6. Calculated for $C_8H_{17}NO_2 \cdot (CO_2H)_2$: C, 48.2; H, 7.7; N, 5.6

EXAMPLE H

Preparation of N-acetyl-4-(2-methylallyloxy)piperidine

This compound was prepared similarly to Example E, starting from N-acetyl-4-hydroxypiperidine and 2-methylallyl chloride, and was distilled and used directly in the next stage. It had a b.p. of 128° C. @ 1 mm.

EXAMPLE I

Preparation of 4-(2-methoxy-2-methyl-n-propoxy)piperidine

This compound was prepared similarly to Example F, starting from N-acetyl-4-(2-methylallyloxy)piperidine and mercuric acetate/methanol. The compound was characterized as the hemioxalate m.p. 208°–210° C.

Analysis %: Found: C, 56.7; H, 9.5; N, 5.9. Calculated for $C_{10}H_{21}NO_2 \cdot \frac{1}{2}(CO_2H)_2$: C, 56.9; H, 9.6; N, 6.0.

EXAMPLE J

Preparation of 4-(2-hydroxy-2-methyl-n-propoxy)piperidine

This compound, m.p. 80°–82°, was prepared similarly to Example G, starting from N-acetyl-4-(2-methylallyloxy)piperidine and mercuric acetate in a mixture of water and tetrahydrofuran.

Analysis %: Found: C, 62.2; H, 11.1; N, 8.3. Calculated for $C_9H_{19}NO_2$: C, 62.4; H, 11.1; N, 8.1.

EXAMPLE K

Preparation of 4-(2-Ethoxy-2-methyl-n-propoxy)piperidine

This compound was prepared similarly to Example F, starting from N-acetyl-4-(2-methylallyloxy)piperidine and mercuric acetate/ethanol followed by basic hydrolysis to remove the N-acetyl group. A sample was converted to the hemi-oxalate salt which was recrystallized from ethyl acetate/methanol, m.p. 184°–185° C.

Analysis %: Found: C, 58.6; H, 9.7; N, 5.8. Calculated for $C_{11}H_{23}NO_2 \cdot \frac{1}{2}C_2H_2O_4$: C, 58.5; H, 9.8; N, 5.7.

EXAMPLE L

Preparation of 4-(2-isopropoxyethoxy)piperidine

This compound was prepared similarly to Example A from N-acetyl-4-hydroxypiperidine and 1-bromo-2-isopropoxyethane. The compound was characterized by spectroscopic techniques.

EXAMPLE M

Preparation of 4-(2-methoxy-n-propoxy)piperidine

This compound was prepared similarly to Example F, starting from N-acetyl-4-allyloxypiperidine and mercuric acetate in methanol. To improve the conversion of starting material to product the mercuric acetate/methanol treatment was repeated twice to give N-acetyl-4-(2-methoxy-n-propoxy)piperidine, which was hydrolyzed in sodium hydroxide and methanol solution to give 4-(2-methoxy-n-propoxy)piperidine. A sample was characterized as the oxalate salt, m.p. 89°–91° C.

Analysis %: Found: C, 49.6; H, 7.9; N, 5.3. Calculated for $C_9H_{19}NO_2 \cdot C_2H_2O_4$: C, 50.2; H, 8.1; N, 5.3.

EXAMPLE N

Preparation of 4-(2-Phenoxy-n-propoxy)piperidine

N-Acetyl-4-(2-hydroxy-n-propoxy)piperidine (12 g.) in dry D.M.F. (50 ml.) was added dropwise to a stirred suspension of sodium hydride (5.0 g., 50% dispersion in mineral oil) in D.M.F. (50 ml.) at 60°–70° C. under an atmosphere of nitrogen. The suspension was stirred for 3 hours, then fluorobenzene (6.4 g.) in D.M.F. (50 ml.) added dropwise and the suspension stirred at 100° C. for 50 hours. The cooled solution was treated with isopropanol (20 ml.) then water (200 ml.), extracted with petroleum ether (3×200 ml.) and chloroform (3×200 ml.). The combined chloroform extracts were dried (Na₂SO₄) and the solvent evaporated in vacuo. The residue (9.0 g.) in sodium hydroxide solution (20 ml., 5N) and methanol (20 ml.) to bring about solution was heated under reflux for 5 hours. The methanol was evaporated, the residue diluted with water then extracted with chloroform (3×50 ml.). The combined chloroform extracts were washed with 2N HCl (3×30 ml.), the combined aqueous extracts basified to pH 12 with sodium hydroxide solution and extracted with chloroform (3×50 ml.). The combined chloroform layers were dried (Na₂SO₄), solvent evaporated in vacuo, then the residue triturated with ether and filtered. The filtrate was concentrated then distilled to give 4-(2-phenoxy-n-propoxy)piperidine (0.5 g.), b.p. 118°–122° C./0.3 mm., characterized spectroscopically.

EXAMPLE O 4-(2-[2,6-Dimethoxyphenoxy]ethoxy)piperidine

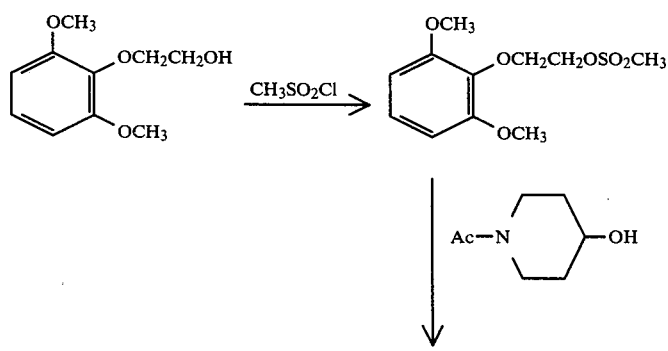

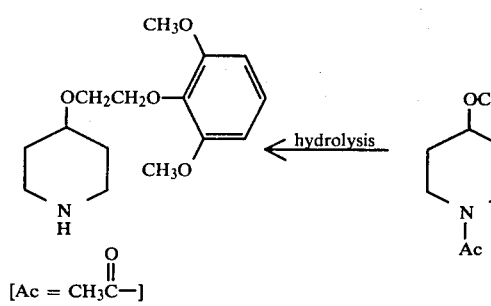 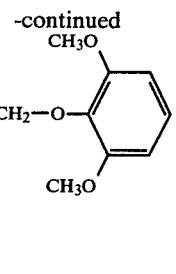

← hydrolysis

[Ac = CH₃C(=O)—]

Methanesulphonyl chloride (23 g.) was added dropwise to a stirred solution of 2-[2,6-dimethoxyphenoxy]ethanol (20 g.) (J. Med. Chem. 1969, 12, 326) in pyridine (50 ml.). The solution was left at room temperature for 60 hours, then the solvent evaporated under reduced pressure. The residue was taken up in chloroform, washed with water (3×100 ml.) and sodium bicarbonate solution (5%, 3×100 ml.), dried and the solvent evaporated. The residue was triturated with n-hexane and the solid collected to give 2-[2,6-dimethoxyphenoxy]-ethyl mesylate (11.3 g.) characterized spectroscopically.

N-Acetyl-4-hydroxypiperidine (4.3 g.) in D.M.F. (50 ml.) was added dropwise to a stirred suspension of sodium hydride (3.0 g., 50% dispersion in mineral oil) in D.M.F. (50 ml.) under an atmosphere of nitrogen. After stirring for 3 hours at room temperature 2-[2,6-dimethoxyphenoxy]ethyl mesylate (9.0 g.) in D.M.F. (50 ml.) was added dropwise and stirring continued for 20 hours at room temperature. The solvent was evaporated in vacuo, the residue taken up in water, extracted with chloroform (3×100 ml.), the organic layer dried (Na₂SO₄) and the solvent evaporated. Distillation gave N-acetyl-4-(2-[2,6-dimethoxyphenoxy]ethoxy)piperidine (6.0 g.), b.p. 200° C. @ 1 mm.

This product (6.0 g.) in methanol (40 ml.) and sodium hydroxide solution (20 ml., 5N) was heated under reflux for 20 hours. Methanol was evaporated under reduced pressure, the aqueous residue extracted with petroleum ether (3×30 ml.) and ether (3×30 ml.). The ether extract was dried (Na₂SO₄) and the solvent evaporated. The residue in ether was treated with ethereal hydrogen chloride and the precipitated solid recrystallized from isopropanol to give 4-(2-[2,6-dimethoxyphenoxy]ethoxy)piperidine hydrochloride (1.4 g.), m.p. 143°–145° C.

Analysis %: Found: C, 56.4; H, 7.6; N, 4.3. Calculated for $C_{15}H_{23}NO_4 \cdot HCl$: C, 56.7; H, 7.6; N, 4.4.

EXAMPLE P (A) Preparation of N-Acetyl-4-(2,2-diethoxyethoxy)piperidine

N-Acetyl-4-hydroxypiperidine (57.2 g.) in dry D.M.F. (250 ml.) was added dropwise to a stirred suspension of sodium hydride (23.2 g., 50% dispersion in mineral oil) in dry D.M.F. (200 ml.) under an atmosphere of nitrogen and with external cooling in an ice/water bath. The suspension was allowed to warm to room temperature then stirred for 5 hours. Bromoacetaldehyde diethylacetal (94.7 g.) was added slowly to the stirred reaction mixture with cooling then the mixture was stirred at room temperature for 18 hours. A further quantity of sodium hydride (23.2 g.) was added portionwise and stirring continued until effervescence had ceased. A further 100 ml. dry D.M.F. was added and the mixture cooled in an ice/water bath while a second batch of bromoacetaldehyde diethylacetal (94.7 g.) was slowly added. The mixture was stirred at room temperature for 3 hours then isopropopanol (150 ml.) added to destroy excess sodium hydride. The suspension was filtered, the filtrate concentrated under reduced pressure then the residue taken up in water and extracted with chloroform. The chloroform extract was dried (Na₂SO₄), the solvent evaporated in vacuo and the residue distilled to give N-acetyl-4-(2,2-diethoxyethoxy)piperidine (61.5 g.), b.p. 142°–145° C./3 mm., characterized by n.m.r.

(B) Preparation of N-Acetyl-4-(2-hydroxyethoxy)piperidine

N-Acetyl-4-(2,2-diethoxyethoxy)piperidine (12 g.) in 0.5 N hydrochloric acid (50 ml.) was stirred at room temperature overnight. The solution was saturated with sodium chloride and extracted several times with chloroform (total 500 mls.). The chloroform extract was dried (Na₂SO₄) and the solvent evaporated in vacuo and with a bath temperature below 30° C. The resultant intermediate aldehyde (9.8 g.) was reduced immediately with sodium borohydride (0.75 g.) in ethanol (75 ml.), at pH 6. After stirring for 3 hours at room temperature reduction was complete. Water was then added to the stirred solution and the organic solvent evaporated in vacuo. The residue was taken up in water (30 ml.), extracted with chloroform (10×30 ml.), the combined chloroform extracts dried (Na₂SO₄) and the solvent evaporated in vacuo. The residue was taken up in water (70 ml.) and washed with petroleum ether (2×10 ml.). The aqueous phase was concentrated to give N-acetyl-4-(2-hydroxyethoxy)piperidine (6.9 g.) characterized spectroscopically. A sample was distilled and had a b.p. of 139°–140° C./0.3 mm.

Analysis %: Found: C, 57.5; H, 9.1; N, 7.6. Calculated for $C_9H_{17}NO_3$: C, 57.8; H, 9.1; N, 7.5.

(C) 4-(2-Cyclopentyloxyethoxy)piperidine

N-Acetyl-4-(2-hydroxyethoxy)piperidine (5.0 g.) in D.M.F. (25 ml.) was added dropwise to a stirred suspension of sodium hydride (1.28 g., 50% dispersion in mineral oil) in dry D.M.F. (50 ml.) under an atmosphere of nitrogen. When effervescence had ceased, cyclopentyl mesylate (4.4 g.) (Tetrahedron 1972, 28, 2469) in D.M.F. (10 ml.) was added slowly and the mixture stirred at room temperature for 40 hours. Additional quantities of sodium hydride (0.64 g.) and then cyclopentyl mesylate (2.2 g.) were added and the mixture stirred at 60° C. for 7 hours, then at room temperature for 64 hours. Isopropanol was added, the mixture filtered and the filtrate concentrated in vacuo. The residue in ethanol (30 ml.) and 5 N sodium hydroxide solution (30 ml.) was heated under reflux for 3 hours. The ethanol was removed in vacuo, the residue diluted with water and extracted with chloroform. The chloroform extract was dried ($Na_2SO_4$), solvent evaporated in vacuo, then the residue in chloroform treated with ethereal hydrogen chloride. The solvent was decanted and the residue triturated with ether to give 4-(2-cyclopentyloxyethoxy)piperidine hydrochloride as a gum. The product contained some 4-(2-hydroxyethoxy)piperidine impurity but was used directly.

EXAMPLE Q

Preparation of 4-(2-p-fluorophenoxyethoxy)piperidine

A solution of N-acetyl-4-(2-hydroxyethoxy)piperidine (5.0 g.), triphenylphosphine (8.4 g.), diethyl azodicarboxylate (5.6 g.) and p-fluorophenol (3.36 g.) in freshly distilled tetrahydrofuran (75 ml.) was stirred in an ice bath for 2 hours and then left at room temperature for 48 hours. Solvent was evaporated in vacuo, the residue taken up in chloroform and washed twice with 1 N sodium hydroxide solution and twice with water, dried ($Na_2SO_4$) and the solvent evaporated in vacuo. The residue was taken up in the minimum volume of refluxing ether, then set aside to cool in a refrigerator. The precipitated solid was collected, the filtrate evaporated and the residue taken up in ether and set aside to cool. The precipitated solid was again removed, the filtrate evaporated and the residue extracted with refluxing petroleum ether (60°–80°, 5×100 ml.). The solvent was evaporated in vacuo and the residue in ethanol (50 ml.) and sodium hydroxide solution (50 ml.) was heated under reflux for 5 hours, then neutralized with 2 N hydrochloric acid and the organic solvent evaporated. The aqueous residue was acidified to pH 2 with 2 N hydrochloric acid and extracted twice with ether. The aqueous phase was basified to pH 12 with 2 N sodium hydroxide solution then extracted with chloroform (3×100 ml.).

The combined chloroform extracts were dried ($Na_2SO_4$) and the solvent evaporated in vacuo to give 4-(2-p-fluorophenoxyethoxy)piperidine (1.3 g.).

A sample of this product in chloroform was converted to the hydrochloride salt by treatment with ethereal hydrogen chloride and had an m.p. 144°–145° C.

Analysis %: Found: C, 56.1; H, 6.8; N, 5.5. Calculated for $C_{13}H_{18}FNO_2.HCl$: C, 56.6; H, 6.9; N, 5.1.

EXAMPLES R TO U

The following piperidine derivatives were prepared by a similar procedure to that of Example Q, starting from N-acetyl-4-(2-hydroxyethoxy)piperidine and the appropriate phenol.

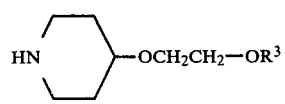

| Example No. | $R^3$ | Form Isolated and m.p. (°C.) | Analysis (Theoretical in brackets) | | |
|---|---|---|---|---|---|
| | | | C | H | N |
| R | —⟨C₆H₄⟩—CH₃ | Hydrochloride 145–146° | 61.4 (61.9 | 8.1 8.2 | 5.1 5.2) |
| S | —⟨C₆H₄⟩—OCH₃ | Hydrochloride 197–198° | 58.3 (58.4 | 7.8 7.7 | 4.6 4.9) |

-continued

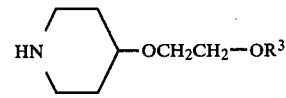

| Example No. | $R^3$ | Form Isolated and m.p. (°C.) | Analysis (Theoretical in brackets) | | |
|---|---|---|---|---|---|
| | | | C | H | N |
| T | —⟨C₆H₄⟩—CF₃ | Oxalate 122–123° | 50.4 (50.7 | 5.3 5.3 | 3.7 3.7) |
| U | —⟨C₆H₄⟩—OCH₃ | Oxalate, 151–153° | 56.2 (56.3 | 6.9 6.8 | 4.2 4.1) |

EXAMPLE V

Preparation of 4-[2-(4-piperidyloxy)ethoxy]benzamide

N-Acetyl-4-(2-hydroxyethoxy)piperidine (1.0 g.), 4-hydroxybenzamide (0.82 g.), diethyl azodicarboxylate (1.12 g.) and triphenylphosphine (1.68 g.) in tetrahydrofuran (30 ml.) were stirred at room temperature for 66 hours. The precipitated solid was collected and dried to give 4-[2-(N-acetyl-4-piperidyloxy)ethoxy]benzamide (0.72 g.), m.p. 154°–155° C.

Analysis %: Found: C, 62.7; H, 7.1; N, 9.1. Calculated for $C_{16}H_{22}N_2O_4$: C, 62.7; H, 7.2; N, 9.2.

4-[2-(N-acetyl-4-piperidyloxy)ethoxy]benzamide (4.3 g.) in ethanol (60 ml.), water (30 ml.) and 2 N hydrochloric acid (10 ml.) was heated under reflux for 24 hours then the solvent evaporated in vacuo. The residue was taken up in water and extracted three times with chloroform, the aqueous phase was adjusted to pH 12 with sodium carbonate solution and extracted three times with chloroform. The combined chloroform extracts were discarded, the aqueous phase was saturated with sodium chloride and extracted with chloroform, the chloroform layer dried ($Na_2SO_4$), and the solvent evaporated in vacuo to give 4-[2-(4-piperidyloxy)ethoxy]benzamide (0.36 g.). The aqueous phase was concentrated in vacuo and the residual solid extracted with refluxing ethyl acetate (200 ml.).

The solid was removed by filtration and the filtrate evaporated in vacuo to give further 4-[2-(4-piperidyloxy)ethoxy]benzamide (0.30 g.) identical with that obtained above. A sample of this product in chloroform/methanol was converted to the hydrochloride salt by treatment with ethereal hydrogen chloride, then recrystallized from ethyl acetate/isopropanol, m.p. 244°–246° C., characterized spectroscopically.

EXAMPLE W

Preparation of 3-[2-(4-Piperidyloxy)ethoxy]benzamide

N-Acetyl-4-(2-hydroxyethoxy)piperidine (5.0 g.), 3-hydroxybenzamide (4.4 g.), diethyl azodicarboxylate (5.6 g.) and triphenylphosphine (8.4 g.) in dry tetrahydrofuran (100 ml.) were stirred at 0° C. for 2 hours then at room temperature for 64 hours. The solvent was evaporated in vacuo, then the residue treated with refluxing ether (3×100 ml.) and the mother liquors decanted. The residual oil was taken up in chloroform and washed with dilute sodium hydroxide solution (40 ml.) and water (40 ml.). The chloroform layer was dried ($MgSO_4$) then the solvent evaporated in vacuo. The residual oil was treated with ether (50 ml.) and set aside in the fridge. The resulting solid was collected, slurried with ether (30 ml.), filtered and the solid washed with ether (30 ml.) to give 4-[2-(N-acetyl-4-piperidyloxy)ethoxy]benzamide (3.7 g.) containing some triphenylphosphine oxide (approximately 25% by n.m.r.).

The product in ethanol (48 ml.), water (24 ml.) and 2 N hydrochloric acid (8 ml.) was heated under reflux for 24 hours then the ethanol evaporated in vacuo. The aqueous residue was extracted with ether (2×100 ml.), then chloroform (100 ml.), then the aqueous phase was adjusted to pH 12 with sodium hydroxide solution and extracted with chloroform (2×100 ml.). The organic layer was dried (MgSO$_4$) and the solvent evaporated in vacuo to give 3-[2-(4-piperidyloxy)ethoxy]benzamide (0.55 g.). The aqueous phase was saturated with sodium chloride and extracted with chloroform (3×100 ml.). The combined chloroform extracts were dried (MgSO$_4$) and the solvent evaporated in vacuo to give a second crop of 3-[2-(4-piperidyloxy)ethoxy]benzamide (0.26 g.) identical with that obtained above. This sample was characterized as the hydrochloride salt by treatment of an ethanol solution with ethereal hydrogen chloride, m.p. 144°–146° C.

Analysis %: Found: C, 56.0; H, 7.2; N, 9.2. Calculated for C$_{14}$H$_{20}$N$_2$O$_3$.HCl: C, 55.9; H, 7.1; N, 9.3.

EXAMPLE X

Preparation of 4-(2-hydroxyphenethyloxy)piperidine

N-Acetyl-4-hydroxypiperidine (5.0 g.) in tetrahydrofuran (THF) (50 ml.) was added to a stirred suspension of sodium hydride (1.84 g., 50% dispersion in mineral oil) in tetrahydrofuran (THF) (25 ml.) under an atmosphere of nitrogen. When effervescence had ceased, styrene oxide (4.6 g.) in THF (25 ml.) was added, then the reaction mixture was diluted with dimethylformamide (DMF) (25 ml.) and stirred at 60° C. for 18 hours. After addition of isopropanol to the cooled solution, the solvent was removed in vacuo, the residue treated with water, adjusted to pH 4 with 2 N hydrochloric acid, and extracted with chloroform. The chloroform extract was dried (Na$_2$SO$_4$) and the solvent evaporated in vacuo to give N-acetyl-4(2-hydroxyphenethyloxy)piperidine. This product in ethanol (50 ml.) and 5 N sodium hydroxide solution (100 ml.) was heated under reflux for 3 hours. The solvent was then removed in vacuo, the residue taken up in water, extracted with chloroform, dried and the solvent evaporated in vacuo. The product in chloroform was converted to the hydrochloride salt by treatment with ethereal hydrogen chloride and evaporation of the solvent.

The residue was taken up in methanol, treated with ether, the precipitated solid separated and recrystallized from isopropanol to give 4-(2-hydroxyphenethyloxy)piperidine hydrochloride (0.6 g.), m.p. 174°–175° C.

Analysis %: Found: C, 60.1; H, 7.8; N, 5.2. Calculated for C$_{13}$H$_{19}$NO$_2$.HCl: C, 60.6; H, 7.8; N, 5.4.

EXAMPLE Y

Preparation of 4-(2-ethoxyphenethyloxy)piperidine

N-Acetyl-4-(2-hydroxyphenethyloxy)piperidine (8.0 g.) and dimethoxyethane (0.3 g.) in dry dimethylformamide (50 ml.) were added dropwise to a stirred suspension of sodium hydride (2.96 g., 50% dispersion in mineral oil) in dry dimethylformamide (50 ml.). The suspension was stirred at room temperature for 3.5 hours, cooled to 0°–5° C. then a solution of ethyl iodide (9.6 g.) in dimethylformamide (25 ml.) added dropwise. The mixture was allowed to warm to room temperature (20° C.), then stirred at room temperature for 2 hours. Isopropanol (75 ml.) was added, the solvent removed in vacuo and the residue partitioned between chloroform and water. The chloroform layer was dried and the solvent evaporated in vacuo to give N-acetyl-4-(2-ethoxyphenethyloxy)piperidine (5.2 g.).

This product in ethanol (50 ml.) and sodium hydroxide solution (50 ml., 5 N) was heated under reflux for 3.5 hours. The organic solvent was removed in vacuo and the aqueous residue extracted with chloroform. The organic extract was dried (Na$_2$SO$_4$), evaporated in vacuo, then the residue partitioned between 2 N hydrochloric acid solution and ether. The aqueous phase was then basified with sodium carbonate solution and extracted with chloroform. The chloroform extract was dried (Na$_2$SO$_4$), the solvent evaporated in vacuo, then the residue was taken up in ether and converted to the oxalate salt. Recrystallization from isopropanol gave 4-(2-ethoxyphenethyloxy)piperidine oxalate salt (1.6 g.), m.p. 136°–137° C.

Analysis %: Found: C, 60.3; H, 7.4; N, 4.1. Calculated for C$_{15}$H$_{23}$NO$_2$.C$_2$H$_2$O$_4$: C, 60.2; H, 7.4; N, 4.1.

EXAMPLE Z

Preparation of 4-(2-ethoxy-1-phenylethoxy)piperidine (i) α-(N-Acetyl-4-piperidinoxy)phenylacetic acid, ethyl ester N-Acetyl-4-hydroxypiperidine (27.5 g.) in dry dimethylformamide (100 ml.) was added slowly to a stirred suspension of sodium hydride (25 g., 50% dispersion in mineral oil) in dimethylformamide (150 ml.) and dimethoxyethane (10 ml.).

The suspension was stirred at room temperature for 3 hours. α-Bromophenylacetic acid (45 g.) in dimethylformamide (250 ml.) was then added slowly with ice/water cooling. The mixture was stirred at room temperature for 20 hours, then isopropanol added and the solvent evaporated in vacuo. The residue was taken up in water, acidified to pH 1 with 2 N hydrochloric acid and extracted 4 times with chloroform (300 ml.). The combined chloroform extracts were washed with water and brine, dried (MgSO$_4$) and the solvent evaporated in vacuo. The residue in anhydrous ethanol (450 ml.) with concentrated sulphuric acid (9 ml.) was heated under reflux for 8 hours. The aqueous residue was adjusted to pH 10 with sodium carbonate solution and extracted twice with chloroform. The combined chloroform extracts were dried (MgSO$_4$) and evaporated in vacuo. Distillation of the residue gave α-(N-acetyl-4-piperidinoxy)phenylacetic acid, ethyl ester (37.2 g.), b.p. 190°–194° C./0.18 mm.

Analysis %: Found: C, 66.4; H, 7.8; N, 4.5. Calculated for C$_{17}$H$_{23}$NO$_4$: C, 66.9; H, 7.6; N, 4.6.

(ii) N-Acetyl-4-(2-hydroxy-1-phenylethoxy)piperidine

Lithium borohydride (3.24 g.) was added portionwise to a solution of α-(N-acetyl-4-piperidinoxy) phenylacetic acid, ethyl ester (11.2 g.) in dry tetrahydrofuran (200 ml.). When the hydrogen evolution had subsided the reaction mixture was heated under reflux for 4 hours. Water was added to the cooled solution, the solvent evaporated in vacuo, then the residue taken up in chloroform (200 ml.) and washed with dilute hydrochloric acid, water and brine. The chloroform extract was dried (MgSO$_4$) and the solvent evaporated in vacuo. Thin layer chromatography analysis of the product indicated that reduction was incomplete, therefore the product in tetrahydrofuran (100 ml.) was treated with a further quantity of lithium borohydride (3.24 g.) and heated under reflux for 4 hours. The reaction mixture was treated as above to give N-acetyl-4-(2-hydroxy-1-phenyl-ethoxy) piperidine (9.5 g.) as an oil which solidified on standing. A sample crystallized from ether and had an m.p. of 92°–94° C.

Analysis %: Found: C, 68.1; H, 8.1; N, 5.7. Calculated for $C_{15}H_{21}NO_3$: C, 68.4; H, 8.1; N, 5.3.

(iii) 4-(B 2-Ethoxy-1-phenylethoxy)piperidine

This compound was prepared similarly to Example Y, starting from N-acetyl-4-(2-hydroxy-1-phenylethoxy)piperidine (prepared as in part (ii) above) and ethyl iodide, followed by basic hydrolysis of the N-acetyl group. A sample was characterized as the oxalate salt, m.p. 137°–139° C.

Analysis %: Found: C, 59.9; H, 7.4; N, 4.0. Calculated for $C_{15}H_{23}NO_2.C_2H_2O_4$: C, 60.2; H, 7.4; N, 4.1.

EXAMPLE AA 4-(2-Phenoxy-1-phenylethoxy)piperidine

N-Acetyl-4-(2-hydroxy-1-phenylethoxy)piperidine (5.25 g.) (prepared as in Example Z (ii)), diethyl azodicarboxylate (4.2 g.), triphenylphosphine (6.3 g.) and phenol (2.25 g.) in dry tetrahydrofuran (100 ml.) were stirred at 0° C. for 2 hours then left at room temperature for 48 hours. The solvent was evaporated in vacuo, the residue taken up in refluxing diethyl ether (50 ml.) and left in a refrigerator overnight. The precipitated by-products were removed by filtration and the filtrate evaporated to dryness. The residue was again taken up in ether, set aside to cool and the precipitated solid filtered off. The ether filtrate was evaporated to dryness and the residue in methanol (50 ml.) and sodium hydroxide solution (30 ml., 5 N) was heated under reflux for 5 hours.

The organic solvent was removed in vacuo, the aqueous residue acidified to pH 3 with 2 N hydrochloric acid and extracted twice with ether. The aqueous phase was adjusted to pH 12 with sodium hydroxide solution and extracted with ether (3×100 ml.). The combined ether extracts were dried (MgSO4) and the solvent evaporated in vacuo to give 4-(2-phenoxy-1-phenylethoxy)piperidine (3.55 g.) as an oil. A sample was converted to the oxalate salt which was recrystallized from isopropanol and had an m.p. of 170°–172° C.

Analysis %: Found: C, 64.9; H, 6.6; N, 3.8. Calculated for $C_{19}H_{23}NO_2.C_2H_2O_4$: C, 65.1; H, 6.5; N, 3.6.

EXAMPLE BB

Preparation of 4-(2-hydroxy-2-phenyl-n-propoxy)piperidine (i) N-Acetyl-4-(2-phenylallyloxy)piperidine N-Acetyl-4-hydroxypiperidine (13.6 g.) in dimethylformamide (50 ml.) was added dropwise to a stirred suspension of sodium hydride (10 g. 50% dispersion in mineral oil) in dimethylformamide (50 ml.) under nitrogen. The mixture was stirred at room temperature for 3 hours then α-(bromomethyl)styrene (20 g.) in dimethylformamide (50 ml.) was added dropwise. The mixture was stirred at room temperature for 4 hours, then diluted with water and extracted with chloroform (3×200 ml.). The combined chloroform extracts were dried (Na2SO4), evaporated in vacuo, and distilled to give N-acetyl-4-(2-phenylallyloxy)piperidine (25 g.), b.p. 170°–180° C./0.3 mm. with an n.m.r. spectrum in accordance with this structure.

(ii) 4-(2-Hydroxy-2-phenyl-n-propoxy)piperidine

N-Acetyl-4-(2-phenylallyloxy)piperidine (4.0 g.) in dry tetrahydrofuran (60 ml.) was added dropwise to a stirred solution of mercuric acetate (6.35 g.) in water (60 ml.) and the solution stirred at room temperature for one hour. Sodium hydroxide solution (40 ml., 3 N) and sodium borohydride (0.75 g.) in sodium hydroxide solution (40 ml., 3 N) were then added dropwise to the stirred solution at 0° C. The grey suspension was stirred at 0° C. for one hour, glacial acetic acid was added to pH 6, then the suspension filtered and the filtrate extracted with chloroform (3×150 ml.). The combined chloroform extracts were dried (Na2SO4) and evaporated in vacuo to give N-acetyl-4-(2-hydroxy-2-phenyl-n-propoxy)piperidine (2.1 g.). This product in methanol (30 ml.) and sodium hydroxide solution (20 ml., 5 N) was heated under reflux for 4 hours. The organic solvent was evaporated and the aqueous solution extracted with chloroform (3×20 ml.), dried (Na2SO4) and the solvent evaporated in vacuo to give 4-(2-hydroxy-2-phenyl-n-propoxy)piperidine (1.8 g.) as an oil. A sample was characterized as the oxalate salt which recrystallized from ethyl acetate and had an m.p. of 132°–134° C.

Analysis %: Found: C, 58.8; H, 7.1; N, 4.8. Calculated for $C_{14}H_{21}NO_2.C_2H_2O_4$: C, 59.1; H, 7.1; N, 4.3.

EXAMPLE CC

Preparation of 4-(2-ethoxy-2-phenyl-n-propoxy)piperidine

N-Acetyl-4-(2-phenylallyloxy)piperidine (7.0 g.) (prepared as in Example BB) in ethanol (10 ml.) was added to a stirred suspension of mercuric acetate (9.2 g.) in ethanol (50 ml.) at room temperature. The mixture was stirred at room temperature for one hour then cooled to 0° C. Sodium hydroxide solution (20 ml., 5 N) followed by sodium borohydride (1.03 g.) in sodium hydroxide solution (20 ml., 5 N) were added to the stirred suspension and after 10 minutes glacial acetic acid was added to pH 6. The suspension was filtered, the filtrate concentrated and the residue partitioned between chloroform and water. The organic layer was dried (Na2SO4) and the solvent evaporated in vacuo. Gas-liquid chromatographic (GLC) analysis of the product indicated incomplete conversion to the desired product therefore the oxymercuration process was repeated as above to give N-acetyl-4-(2-ethoxy-2-phenyl-n-propoxy)piperidine (7.4 g.), 84% pure by GLC. The product in ethanol (100 ml.) and sodium hydroxide solution (30 ml.) was heated under reflux for 11 hours. The organic solvent was evaporated and the aqueous solution was extracted with chloroform (3×30 ml.). The combined chloroform extracts were dried (Na2SO4) and the solvent evaporated in vacuo to give 4-(2-ethoxy-2-phenyl-n-propoxy)piperidine as an oil (3.8 g.). A sample was converted to the oxalate salt which was recrystallized twice from ethyl acetate then acetone and had an m.p. of 126°–127° C.

Analysis %: Found: C, 60.4; H, 7.6; N, 4.1. Calculated for $C_{16}H_{25}NO_2.C_2H_2O_4.\frac{1}{4}H_2O$: C, 60.4; H, 7.3; N, 3.9.

We claim:

1. A compound selected from the group consisting of those of the formula

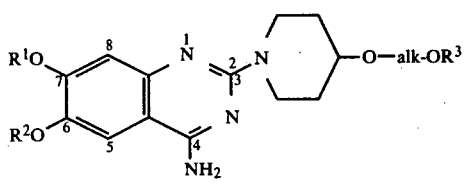

(I)

and the pharmaceutically-acceptable acid addition salts thereof, wherein $R^1$ and $R^2$ are selected from the group consisting of $C_{1-4}$ alkyl and $—CH_2CF_3$; alk is selected from the group consisting of ethylene, monophenyl substituted ethylene, mono- and dimethyl substituted ethylene, and monophenyl-monomethyl substituted ethylene; and $R^3$ is selected from the group consisting of hydrogen, $C_{1-4}$ alkyl, $C_3$–$C_6$ cycloalkyl, and

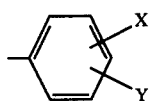

wherein each of X and Y is selected from the group consisting of hydrogen, $C_{1-4}$ alkyl, $C_{1-4}$ alkoxy, halogen, $CF_3$, $—CONR^4R^5$ and $—SO_2NR^4R^5$ wherein each of $R^4$ and $R^5$ is selected from the group consisting of hydrogen and $C_{1-4}$ alkyl.

2. A compound according to claim 1 wherein each of $R^1$ and $R^2$ is methyl;
—O-alk-$OR^3$ is selected from the group consisting of:
—O—$CH_2CH_2$—$OR^3$,
—O—$CH_2$—$CH(CH_3)$—$OR^3$,
—O—$CH_2C(CH_3)_2$—$OR^3$,
—O—$CH_2$—$CH(C_6H_5)$—$OR^3$ and
—O—$CH(C_6H_5)CH_2$—$OR^3$;
$R^3$ is selected from the group consisting of hydrogen, $C_{1-4}$ alkyl, $C_{3-6}$ cycloalkyl, and

wherein each of X and Y is selected from the group consisting of hydrogen, $C_{1-4}$ alkyl, $C_{1-4}$ alkoxy, fluoro and carbamoyl.

3. A compound according to claim 2 wherein $R^3$ is hydrogen or alkyl.

4. The compound according to claim 3 wherein -O-alk-$OR^3$ is —$OCH_2CH_2OR^3$ and $R^3$ is ethyl.

5. A compound according to claim 2 wherein $R^3$ is

6. The compound according to claim 5 wherein -O-alk-$OR^3$ is —$OCH_2CH_2OR^3$ wherein $R^3$ is phenyl.

7. The compound according to claim 2 wherein -O-alk-$OR^3$ is —O—$CH(C_6H_5)CH_2$—$OR^3$ wherein $R^3$ is phenyl.

8. A compound according to claim 2 wherein -O-alk-$OR^3$ is —O—$CH_2$—$CH(C_6H_5)$—$OR^3$ wherein $R^3$ is $C_{1-4}$ alkyl.

9. The compound according to claim 8 wherein $R^3$ is ethyl.

10. A pharmaceutical composition comprising an antihypertensive amount of a compound of claim 1 together with a pharmaceutically acceptable diluent or carrier.

11. A method for treating hypertension in an animal which comprises administering to said animal an antihypertensive amount of a compound according to claim 1.

* * * * *